United States Patent [19]

Loria

[11] Patent Number: 5,478,566
[45] Date of Patent: Dec. 26, 1995

[54] STIMULATION OF CYTOKINE PRODUCTION

[76] Inventor: Roger M. Loria, 3219 Brook Rd., Richmond, Va. 23227

[21] Appl. No.: 128,298

[22] Filed: Sep. 29, 1993

[51] Int. Cl.$^6$ ........................................ A61F 13/00
[52] U.S. Cl. ..................... 424/449; 424/85.1; 424/85.2; 424/443
[58] Field of Search ................... 424/85.2, 85.1, 424/449, 443

[56] References Cited

U.S. PATENT DOCUMENTS

| | | | |
|---|---|---|---|
| 4,978,532 | 12/1990 | El-Rashidy | 424/448 |
| 5,077,284 | 12/1991 | Loria | 514/171 |
| 5,206,008 | 4/1993 | Loria | 424/45 |
| 5,277,907 | 1/1994 | Loria | 424/93 V |

OTHER PUBLICATIONS

Daynes, R. A. et al Eur. J. Immunol., 1990 vol. 20, pp. 793–802.
Meikle, A. W. et al J. Steroid Biochem Molec Biol., 1992, vol. 42, pp. 293–304.
Suzuki, T. et al. Clin. Immunol and Immuno–pathology, 61, pp. 202–211, 1991.

*Primary Examiner*—D. Gabrielle Phelan
*Attorney, Agent, or Firm*—Glenna Hendricks; Stephen Gates

[57] ABSTRACT

$3\beta,7\beta,17\beta$-androstenetriol ("$\beta$AET") may be used to increase production of IL-2 in cell culture and in the intact animal. Increase in IL-2 under stimulating effect of $\beta$AET provides benefits associated with IL-2 administration without the untoward effects such as increased cortisol production.

12 Claims, No Drawings

5,478,566

STIMULATION OF CYTOKINE PRODUCTION

FIELD OF THE INVENTION

This invention relates to 3β,17β-androstenediol ("βAED") and 3β,7β,17β-androstenetriol ("βAET") and their use to counteract the antiproliferative and immunosuppressive effects of hydrocortisone and other corticosteroids (i.e., to act as buffers to counteract the lymphosuppressive response to such steroids). βAED and βAET act as immune regulating steroids in the body. By "immune regulating steroids" is meant steroids which mediate immune response to provide the body protection against immune down-regulation. The invention also relates to means for testing analogues of βAED and βAET to compare the effectiveness of such analogues as buffers of certain effects of hydrocortisone and other corticosteroids, including immune response and proliferative effects. Finally the invention relates to production of cytokines, including most particularly IL-2 and IL-3, by addition of βAET and its analogues to the growth media of cell cultures of lymphatic cells.

BACKGROUND OF THE INVENTION

In vertebrates the development of host protection against pathogens requires a selective host immune response that involves the mobilization of the humoral and/or cellular mediated immune responses. Several factors adversely affect the body's protective response capability by causing prolonged immuno-suppression or "down-regulation" of the immune system. It is, in reality, more appropriate to speak of "mal-regulation" or "deregulation" of the immune system than of down-regulation since the result is a failure to protect the body from assault. Immuno-suppression provides an opportunity for pathogens to grow in the host. It does not matter what causes the primary insult to immunity. The resulting inability to muster the appropriate immune response has the same effect. Among the many different causes of immuno-suppression are viral, bacterial, fungal, yeast and parasitic infections, chemotherapy, irradiation, severe stress, chronic fatigue syndrome, diabetes mellitus, autoimmune diseases, rheumatoid arthritis and some forms of steroid therapy.

It has long been known that patients receiving steroid hormones of adrenocortical origin at pharmacologically appropriate doses show increased incidence of infectious disease. A. S. Fauci, *Immunolo. Rev.*, 65, 133–155 (1982); and J. E. Parillo and A. S. Fauci, *Annual Review of Pharmacology and Toxicology*, 19, 179–201 (1979). Dehydroepiandrosterone, also known as 3β-hydroxyandrost- 5-en-17-one or dehydroiso-androsterone (referred to hereinafter as DHEA), is a 17-ketosteroid which is quantitatively one of the major adrenocortical steroid hormones found in mammals. M. E. Windholz, *The Merck Index*, Ninth Edition (1976); K. Diem and C. Lentner, *Geigy Scientific Tables* (1975). (Although DHEA appears to serve as an intermediary in gonadal steroid synthesis, the primary physiological function of DHEA has not been fully understood. It has been known, however, that levels of this hormone begin to decline in the second decade of life, reaching 5% of the original level in the elderly.)

Clinically, DHEA has been used systemically and/or topically for treating patients suffering from psoriasis, gout, hyperlipemia, and it has been administered to post-coronary patients. (W. Regelson et al., *New York Academy of Sciences*, 518, 260–273 (1988)). In mammals DHEA has been shown to have weight optimizing and anticarcinogenic effects.

DHEA has been used clinically in Europe in conjunction with estrogen as an agent to reverse menopausal symptoms and also has been used in the treatment of manic depression, schizophrenia, and Alzheimer's disease. DHEA has also been used clinically at 40 mg/kg/day in the treatment of advanced cancer and multiple sclerosis. Mild androgenic effects, hirsutism, and increased libido were the side effects observed. These side effects can be overcome by monitoring the dose and/or by using analogues.

U.S. Pat. No. 5,077,284 entitled "Use of Dehydroepiandrosterone to Improve Immune Response" describes the subcutaneous or oral administration of DHEA to improve the host's response to infections. U.S. Pat. No. 4,978,532 describes use of patch technology to deliver DHEA.

It is now disclosed that DHEA is a precursor in a metabolic pathway which ultimately leads to more powerful agents that increase immune response in mammals. That is, DHEA acts as a biphasic compound: it acts as an immunomodulator when converted to androstenediol (androst-5-ene-3β,17β-diol, βAED) or androstenetriol (androst-5-ene-3β,7β,17β-triol, βAET). However, in vitro DHEA has certain lymphotoxic and suppressive effects on cell proliferation prior to its conversion to βAED and/or βAET. It is, therefore, postulated that the superior immunity enhancing properties obtained by administration of DHEA result from its conversion to more active metabolites.

An agent that would advance the protective regulation of the immune system without giving rise to undesirable side effects seen with DHEA administration would provide particularly advantageous improvement of host resistance against infection. Protective regulation of the immune system could then be effected using lower doses of the chemotherapeutic agent, and would provide more immediate response with a wider range of protection. It has previously been disclosed in U.S. patent application 07/739,809 (now U.S. Pat. No. 5,206,008 incorporated herein in its entirety) that βAED and βAET (asteroid found in the skin, other epithelial tissue and neuronal tissue) enhance immune response and lymphocytic cell proliferation.

DESCRIPTION OF THE INVENTION

In U.S. patent application 07/739,809 (now U.S. Pat. No. 5,206,008) a new class of steroids which act as immune regulators has been identified. 3β,17β-androstenediol (βAED) and 3β,7β,17β-androstenetriol (βAET) have been shown to enhance immune response in the presence of stress, including infection and exposure to chemotherapy. It is believed that 3β,17β-androstenediol (βAED) is converted in the skin to 3β,7β,17β-androstenetriol (βAET) and 3β,7β,17β-androstenetriol (αAET). Both the βAED and βAET have been shown to be potent immune regulators, with the βAET being about 100 times as potent as βAED.

The present invention provides methods of testing the effect of immune-regulating steroids by measuring the counteracting effect of βAED and βAET and their analogues against the antiproliferative effects of corticosteroids in vitro. The method is particularly useful for evaluating the effectiveness of analogues of βAED and βAET and other immune-regulating steroids as buffers of corticosteroid activities. Uses of βAED and βAET have been disclosed in U.S. patent application 07/739,809. These compounds have use as immune regulating steroids for several purposes, as described below. A second aspect of the invention is the use of βAED and βAET in conjunction with corticosteroids to ameliorate some of the undesirable effects of corticosteroid therapy. It has been found in vivo that the spleen and thymus of animals under stress decrease in size. It was found that βAED and βAET do not effect a change in the size of the spleen of normal, healthy animals, but protected the spleen and thymus from involution in animals during infection or other conditions of stress. In spleen cell cultures exposed to hydrocortisone a decrease in proliferation is seen. Spleen lymphocytes in culture, when exposed to mitogens such as concanavalin A (Con A), lipopolysaccharide A (LPS), or some antigens, undergo a marked proliferative increase. Addition of hydrocortisone to such a culture prevents such proliferative response. The addition of βAED and βAET to cultures containing proliferating-inhibiting amounts of hydrocortisone has now been found to counteract or buffer the anti-proliferative effects of corticosteroids such as hydrocortisone. βAED or βAET may be given concurrently with corticosteroids or may be administered in a composition containing a combination of βAED or βAET with corticosteroids.

In addition to their use as immune regulators, βAED and βAET, their esters and other analogues are useful for production of interleukin-3 (IL-3) in cell culture, including autogenous IL-3, as well as other cytokines which are effective in regulation of the body's responses. IL-3 is an important cytokine capable of stimulating granulopoiesis, erythropoiesis and thrombopoiesis. It is a major factor governing differentiation and proliferation of hematopoietic cells. Presently several forms of IL-3 are available. Recombinant human IL-3 has been produced in several organisms. (See U.S. Pat. No. 5,128,450, which is incorporated herein by reference.) However, IL-3 obtained from non-human sources has caused unacceptable side effects.

It has been disclosed in co-pending application 07/739, 809 that βAED and βAET, their esters and analogues, provide means for regulating the immune response, for ameliorating effects of stress, and for avoiding untoward effects of chemotherapy or exposure to irradiation by administration of androstenediol (βAED) and androstenetriol (βAET). The improved means of regulating immune response to viral, bacterial, and other infections can be utilized in treating not only infectious diseases, but also in treating other immune disturbances such as diabetes and chronic fatigue syndrome (both diseases now considered to be immune response related syndromes), rheumatoid arthritis and autoimmune responses. In the case of virus-induced heart or pancreatic infection where no other antiviral chemotherapeutic modality exists, βAED and βAET and their analogues, including esters thereof, have value as prophylactic protective agents.

In clinical medicine, treatment with βAED and βAET can lower morbidity in patients exposed to pathogenic organisms. These agents can be effectively used prophylactically in patients known to be particularly susceptible to infection. Patients undergoing surgery or chemotherapy or patients suffering from burns, hypoplastic or aplastic anemias, or diabetes are such susceptible patients who would benefit from prophylactic administration of βAED and/or βAET. Also among the causes of immuno-suppression treatable with βAED and βAET are viral, bacterial, fungal, yeast and parasitic infections, chemotherapy, irradiation, severe stress, chronic fatigue syndrome and untoward effects of steroid therapy. The compositions of the invention are particularly useful for treating patients suffering from infections caused by viruses that destroy the body's immune response, such as human immunodeficiency virus (HIV) and hepatitis. The protective value of βAED and βAET is particularly important to patients undergoing "dirty" procedures such as bowel surgery or repair of gunshot wounds of the abdomen where pseudomonas presents a serious threat. Patients with a history of conditions such as rheumatic fever would also benefit from prophylactic and maintenance use of the regulatory steroids βAED and βAET or in conjunction with other steroids as disclosed herein. In treating any condition wherein both inflammation and threat of infection are present, treatment with a combination of βAED or βAET or their analogues in conjunction with corticosteroids (both natural and synthesized analogues) can provide benefit of anti-inflammatory action and modification of allergenic response coupled with avoidance of increased susceptibility to infection.

Both βAED and βAET are steroids and possess lipophilic characteristics. Solvents for lipophilic steroids are known in the art and would be used as carriers for these compounds. Examples of such carriers are pharmaceutically acceptable glycols, and cyclodextrins, especially the intrinsically amorphous cyclodextrins. Other vehicles that should be considered include fatty acid esters such as esters of polyoxyethylene sorbitan (Tweens) or sorbitan (Spans) to prepare oil-in-water emulsions. For subcutaneous administration to animals used in the examples, the agents were dissolved 1:1 dimethyl sulfoxide (DMSO)/ethanol, then diluted for subcutaneous administration to the animals. When the compositions were administered by mouth, βAED and βAET were added (without being dissolved) to the diet to provide a composition containing 0.4% βAED. The compositions may be provided in capsules formulated with the usual fillers. For application to the skin, βAED or βAET may, for example, be dissolved in carrier material containing DMSO and alcohol, then applied to a patch or directly to epidermal tissues. For vaginal or rectal administration, βAED or βAET may be administered by suppository, enema, or by application of creams, etc. Compositions of the invention may be administered by any method that will result in contact of the active agent with tissue of ectodermal origin.

βAED and βAET have been found to inhibit the adherence properties of body cells. The anti-adherence properties of the active agents of the invention may be delivered directly to epithelial tissue during surgery. An example of such use would involve the application of compositions containing the active agents of the invention to the omentum in conditions such as infection, endometritis and malignancies of the bowel and ovary wherein adherence of foreign cells or particles to normal cells of the peritoneal lining is a problem. Compositions of the invention may, for example, be administered as mists or sprays. Compositions can also be administered intrathecally.

βAED has previously been used as a laboratory chemical and is available commercially for that purpose from Sigma. A compound now known to have been βAET was produced by Butenandt as an intermediate in preparation of compounds of the androstane and pregnane series. No disclosure of any other use for βAET is seen therein (See Butenandt et al., U.S. Pat. No. 2,170,124, and Ber. 71B, 1316–22 (1938) which are incorporated herein by reference in their entirety.)

Evaluation of the immune regulating effect of steroids can be accomplished using the methods of the invention. By the method disclosed herein it is possible to evaluate the relative potency and relative immediacy of response of analogues of βAED and βAET. The evaluative method relies on the buffering of lymphosuppressive activity of corticosteroids by βAED and βAET and their analogues. The invention provides means of evaluating (1) the ability of βAED, βAET and their analogues to buffer or counteract lymphosuppressive steroids in the presence of lymphocyte-proliferative agents such as concanavalin A and (2) the ability of βAED and βAET to stimulate production of cytokines, especially IL-3 and IL-2. Interestingly, the increased production of IL-2 and IL-3 that is effectuated by activity of βAET appears to simultaneously buffer the increase in cortisol levels that arose from IL-2 levels. These two separate effects differ from each other in their function and characteristics.

Another aspect of the invention is a method of evaluating corticosteroid buffering effect of an agent by growing cultures of cells of lymphoid origin in growth medium containing a mitogen, then dividing the cultures into three subsets. To one subset is added a corticosteroid; to a second subset is added an agent believed to have corticosteroid buffering activity; and to the third subset are added both the corticosteroid added to the first subset and the compound believed to have corticosteroid buffering activity that has been added to the second subset of cultures. After incubation of all subsets for a sufficient period of time to allow cell proliferation, the proliferation in all subsets is measured and compared. If the proliferation seen in cultures of subset 3 is greater than that seen in subset 2, it can be presumed that the test agent has corticosteroid buffering effect. The proliferation may be measured in any manner known in the art. However, use of radioactive markers is a convenient means of evaluating proliferation. [$^3$H]-thymidine is a particularly useful marker for these purposes.

The corticosteroidal compounds used as described herein may be natural corticosteroids or analogues thereof including but not limited to hydrocortisone (cortisol), corticosterone, aldosterone, ACTH, triamcinolone and its derivatives (particularly the diacetate, hexacetonide, and acetonide), betamethasone and its derivatives (including particularly the dipropionate, benzoate, sodium phosphate, acetate, and valerate), flunisolide, prednisone and its derivatives, fluocinolone and its derivatives (particularly the acetonide), diflorasone and its derivatives (particularly the diacetate), halcinonide, dexamethasone and its derivatives (particularly the dipropionate and valerate), desoximetasone (desoxymethasone), diflucortolone and its derivatives (particularly the valerate), flucloronide (fluclorolone acetonide), fluocinonide, fluocortolone, fluprednidene and its derivatives (particularly the acetate), flurandrenolide (flurandrenolone), clobetasol and its derivatives (particularly the propionate), clobetasone and its derivatives (particularly the butyrate), alclometasone, flumethasone and its derivatives (particularly the pivalate), and fluocortolone and its derivatives (particularly the hexanoate).

EXAMPLES OF SYNTHETIC METHODS

SYNTHESIS OF 3β,7β,17β-TRIHYDROXYANDROST-5-ENE (I):

βAET was synthesized using 3β,17β- diacetoxyandrost-5-ene as a starting material. Chromic oxide oxidation of 3β,17β-diacetoxyandrost- 5-ene in glacial acetic acid by the method of Butenandt (op. cit.) gave 3β,17β-diacetoxyandrost-5-en-7-one, (III), the intermediate for preparation of (I). Aluminum isopropoxide reduction of (III)in isopropanol by the method of Butenandt gave (I).

PREPARATION OF 3β,17β-DIACETOXYANDROST-5-EN-7-ONE (III)

37.4 g (0.1 mol) 3β,17β-diacetoxyandrost-5-ene (Steraloids A7850) in 400 ml glacial acetic acid was reacted with 30.06 g (0.3 mol) chromium(VI) oxide (Aldrich 23,265-3) dissolved in 20 ml $H_2O$ and 20 ml glacial acetic acid by the method of Butenandt (op. cit.). The $CrO_3$ solution was added dropwise over 4 hours to the 3β,17β-diacetoxyandrost-5-ene solution while maintaining the temperature at 55° C. At the end of that time methanol was added to the reaction mixture in order to decompose any unreacted $CrO_3$, followed by aqueous salt solution and ether. Evaporation of the ether yielded 7.8 g (20% yield) of crude III. Crystallization from 95% EtOH yielded (III) m.p. 214°–215° C. [218°–219° C., Butenandt, op. cit.; 224°–225° C. (from methanol), Pearson et al., J. Chem. Soc. Perkin Trans., I, 267–273 (1985)] DSC peak 191°–224° C., max at 220° C. Normal phase tlc: EtOAC-cyclohexane-EtOH (45:45:10), Rf=0.86. IR bands: 1737, 1666 cm$^{-1}$, (Pearson, op. cit 1728, 1668).

$^1$H NMR (CDCl3), (d), ppm: 0.81(s,3H), 1.25 (s,3H), 2.02(s,6H), 2.25(m,H at C-4), 2.5(m,H at C-8),4.6(t,H at C-17),4.7(m,H at C- 3), 5.72(s,1H) [Pearson, op. cit. o.80(s, 3H), 1.20(s,3H), 2.03(s,6H), 4.62(m,1H), 5.71(g,1H)] Reverse phase lc/ms (fast atom bombardment detection) detected m/z 389(M+HJ') ion in the major lc peak [Pearson, op. cit. m/z 388(M)].

PREPARATION OF 3β,7β,17β-TRIHYDROXYANDROST-5-ENE (I)

3β,17β-diacetoxyandrost-5-en-7-one was reduced with aluminum isopropoxide in isopropanol by the method of Butenandt (op. cit.) to give 3β,7β,7β-trihydroxyandrost-5-ene. Lithium tri(sec-butyl) borohydride reduction of (III) in tetrahydrofuran to produce (II) was carried out using the same reaction conditions given by Morisaki et al., Chem. Pharm. Bull., 35(5), 1847–52 (1987) for the preparation of 7α-hydroxycholesterol.

PREPARATION OF 3β,7α,17β-TRIHYDROXYANDROST-5-ENE(II)

5.1 ml (5.1 mmol) lithium tri(sec-butyl)borohydride (Aldrich L-Selectride) in tetrahydrofuran was rapidly added to 499 mg (1.28 mmol) of 3β,17β-diacetoxyandrost-5-en-7-one in 15 ml of freshly distilled tetrahydrofuran under nitrogen while stirring for 1.5 hours at ice-bath temperature. 0.9 g KOH in 15 ml methanol was added, the reaction mixture refluxed for 0.5 hours, and then added 37.5 ml of 10% NaCl solution was added. After cooling in freezer(–20°), crystals formed which were filtered to yield 123.6 mg (19%) (II), m.p. 239°–45° C. Crystallization from methanol yielded (II), m.p. 249.5°–253° C. $^1$H nmr (CD(OD)$_3$), (d), ppm: 0.75(s,3H),1.01(s,3H), 3.1(m, 1H), 3.6(t,1H),3.7(d, 1H),5.50(d, 1H). C-13 nmr, (d),ppm assignments (CD(OD)$_3$) are:

| Carbon ppm | | | | | | | | | | | | | | | | | | |
|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 |
| 37.49 | 32.12 | 72.01 | 42.91 | 146.75 | 124.88 | 65.46 | 39.09 | 43.58 | 38.55 | 21.49 | 30.65 | 93.65 | 45.35 | 38.13 | 42.57 | 82.30 | 11.57 | 19.53 |

DISCUSSION

Stereochemistry was assigned to 3β,7β,17β-trihydroxyandrost-5-ene (I) and 3β,7α,17β-trihydroxyandrost-5-ene (II) by comparison of their proton nmr with cholest-5-ene-3β,7β-diol and cholest-5-ene-3β,7α-diol proton nmr [Smith et al., J. Org. Chem., 38, 119–123 (1973)].

PREPARATORY METHOD #2

A second method of preparing βAET has been developed which also used 3β,17β diacetoxyandrost-5-ene as a starting material as before. This compound was oxidized with t-butylhydroperoxide in the presence of chromium hexacarbonyl ($Cr(CO)_6$) to form 3β,17β-diacetoxyandrost- 5-en-7-one as described by Pearson [Pearson, et al., J. Chem Soc. Perkin Trans, I, 267 (1985)]. The enone formed then was reduced with triisobutylaluminum (TIBA) to give the acetylated 7β-hydroxy (I) product.

PREPARATION OF 3β,7β,17β-TRIHYDROXYANDROST-5-ENE

A solution of 3β,17β diacetoxyandrost-5-en-7-one (0.9581 g, 2.466 mmol) and pentane (30 ml), dried over $MgSO_4$) were mixed under a nitrogen atmosphere. TIBA (9.5 ml, 9.5 mmol, 1M in toluene) was then added dropwise by syringe. The solution was stirred at room temperature for about 1 hour. The reaction was terminated by the addition of diluted hydrochloric acid (approximately 5 ml). This solution was added to water (100 ml) and extracted with ethyl acetate (3 times with 50 ml). The organic layers were combined and then washed several times with saturated sodium bicarbonate solution (50 ml), saturated sodium chloride solution (two times with 50 ml,) and water (50 ml). The organic layer was dried over magnesium sulfate and the solvent removed by rotary evaporation to yield 86% crude product. $^1H$ NMR indicated that the crude product contained 3β,17β-diacetoxy-7-β-hydroxyandrost- 5-en-7-one (86%) and 3β,17β-diacetoxy-7α-hydroxyandrost- 5-ene.

The final product I was recovered from another preparation by saponification of the mixed acetate by adding a solution of $K_2CO_3$ in methanol/water to the crude product. The solution was stirred at room temperature and monitored by TLC every hour (TLC conditions—0.25 mm silica gel on glass, solvent system—60% ether, 20% hexane, 15% methanol, 5% water, developed with $I_2$ chamber). The reaction was stopped when only one spot was detected (approximately 5 hr, depending on the $K_2CO_3$ concentration). Dilute acid was added to the reaction mixture until it was slightly acidic. The reaction mixture was worked up by extraction with ethyl acetate (3×50 ml), and the combined organic extracts were washed with saturated NaCl solution (2×50 ml), and then water (1×50 ml). The organic solution was dried over $Mg_2SO_4$ and the solvent removed by evaporation. Recrystallization from 95% ethanol/ethyl acetate mixture gave (I), m.p. 232°–234° C. (lit. 236° C., Butenandt, op. cit.)

βAED and βAET may be substituted with protective groups which yield βAED or βAET on hydrolysis in order to prolong their activity. Hence, acylated and alkylated derivatives are useful as materials which act as precursors to βAED and βAET. Suitable derivatives include but are not limited to compounds of the general formula:

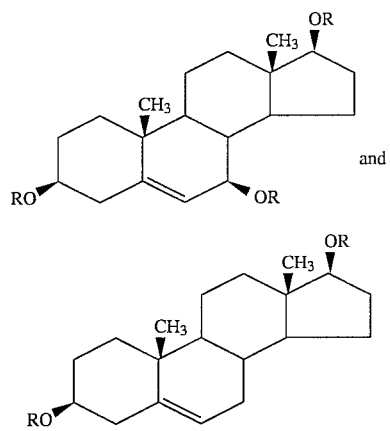

wherein each R individually may be H, alkenyl of 2–8 carbons, alkyl of 1–8 carbons, phenylalkyl of 1–4 carbons, phenyl, or $COR_2$ (acyl), wherein $R_2$ is H, alkyl of 1–8 carbons, alkenyl of 2–8 carbons, phenylalkyl wherein the alkyl has 1–4 carbons (including benzyl) or phenyl. Any phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized.

EXPERIMENTAL

Cultures of spleen cells used for testing properties of the products of the invention were prepared according to the following procedure:

Lymphocytes were harvested from spleens of BALB/c mice. The lymphocytes were set at a concentration of $5.0 \times 10^6$ cells/ml in RPMI 1640 containing 10% fetal calf serum (FCS), 200 μM L-glutamine, 20 mM Hepes, 2.5 U/ml penicillin, 2.5 μg/ml streptomycin, and $5.0 \times 10^{-5} M$ 2-mercaptoethanol. The active agents in amounts designated in the table were added to cultures of the cells in standard 96-well plates in the RPMI 1640 media in 100 μl samples in triplicate. The steroids were dissolved in a 50:50 mixture of dimethyl sulfoxide (DMSO) and ethanol before addition to the cultures. Because the 50:50 DMSO-ethanol mixture used to dissolve the steroids has a suppressive effect on cell proliferation, all results were compared to standard cultures containing 0 2% of the solvent mixture.

EXAMPLE 1

Effects of Added βAED, βAET and Hydrocortisone on Proliferation in the Absence of a Mitogen A series of tests was run in triplicate using BALB/c spleen cells to demonstrate the effect of the products of the invention and hydrocortisone ("Hycort") on cellular proliferation in the absence of a mitogen. Cultures of spleen cells were prepared by the procedure outlined above and steroids were added as shown in Table 1. Twenty four hours after setup, 50

μCi [$^3$H]-thymidine was added to each cell. Four to six hours later, the cells were harvested and counted on a scintillation counter. The results are set forth in Table 1.

TABLE 1

MITOGEN INDUCED BALB/C SPLEEN CELL PROLIFERATION: EFFECTS OF BAET, BAED, AND HYDROCORTISONE

| Steroid | | Average count | St. Dev. |
|---|---|---|---|
| none, no solvent | | 2800 | 200 |
| none, 0.2% DMSO:EtOH | | 2500 | 200 |
| AET 5.0 μM | | 2900 | 1000 |
| AET 0.5 μM | | 6000 | 500 |
| AED 5.0 μM | | 4900 | 1300 |
| AED 0.5 μM | | 4100 | 600 |
| | Hycort 5.0 μM | 3000 | 2300 |
| | Hycort 0.5 μM | 4900 | 1200 |
| AET 5.0 μM | Hycort 5.0 μM | 3400 | 1500 |
| AET 0.5 μM | Hycort 5.0 μM | 2800 | 1300 |
| AED 5.0 μM | Hycort 5.0 μM | 1800 | 500 |
| AED 0.5 μM | Hycort 5.0 μM | 2000 | 700 |

TABLE 1-continued

MITOGEN INDUCED BALB/C SPLEEN CELL PROLIFERATION: EFFECTS OF BAET, BAED, AND HYDROCORTISONE

| Steroid | | Average count | St. Dev. |
|---|---|---|---|
| AET 5.0 μM | Hycort 0.5 μM | 1500 | 500 |
| AET 0.5 μM | Hycort 0.5 μM | 2200 | 300 |
| AED 5.0 μM | Hycort 0.5 μM | 2200 | 1500 |
| AED 0.5 μM | Hycort 0.5 μM | 4300 | 2300 |

The solvent-containing control averaged about 2800±200 counts while the cultures to which steroids had been added ranged from a low of about 1500±500 to about 6000±500 counts. These results do not allow making a determination that there was a significant effect on proliferation from the addition of the steroids to the cultures. Therefore it was concluded that βAED, βAET and corticosteroids have little effect on cellular proliferation in the absence of the stimulus created by mitogens and/or mitogens.

EXPERIMENT 2

Effects of Added βAED and Hydrocortisone on Proliferation in the Presence of a Mitogen Another series of cultures was run adding βAED and/or hydrocortisone to cultures to which concanavalin A had been added in a manner similar to those of Example 1. Preliminary tests on cultures to which concanavalin A had been added at concentrations of 10.0, 5.0, 2.5 and 1.0 μg/ml showed that proliferation of cultures was most sensitive to the effect of added hydrocortisone when the concanavalin A concentration was 2.5 μg/ml, so all tests on the effects of βAED on cultures stimulated with concanavalin A were performed with concanavalin A at 2.5 μg/ml. The results are set forth in Table 2.

TABLE 2

Influence of BAED and Hydrocortisone on Spleen Cell Cultures from BALB/c Mice Stimulated with 2.5 μg/ml Concanavalin A

| AED Concentration | Hycort Concentration | Average count (3 samples) | Standard Deviation | % Reduction of Control |
|---|---|---|---|---|
| 0.2% DMSO:EtOH | | 424,000 | 14,000 | — |
| 5.0 μM | — | 373,000 | 18,000 | 12 |
| 1.0 μM | — | 430,000 | 31,000 | incr. 2 |
| 0.5 μM | — | 426,000 | 21,000 | incr. 1 |
| 0.1 μM | — | 469,000 | 29,000 | incr. 11 |
| 0.05 μM | — | 448,000 | 23,000 | incr. 6 |
| — | 5.0 μM | 216,000 | 26,000 | 49 |
| — | 1.0 μM | 250,000 | 13,000 | 41 |
| — | 0.5 μM | 251,000 | 15,000 | 41 |
| — | 0.1 μM | 262,000 | 22,000 | 38 |
| — | 0.05 μM | 361,000 | 11,000 | 15 |
| 5.0 μM | 1.0 μM | 191,000 | 21,000 | 55 |
| 1.0 μM | 1.0 μM | 230,000 | 16,000 | 46 |
| 0.5 μM | 1.0 μM | 201,000 | 15,000 | 53 |
| 0.1 μM | 1.0 μM | 228,000 | 6,000 | 54 |
| 0.05 μM | 1.0 μM | 238,000 | 18,000 | 44 |
| 5.0 μM | 0.1 μM | 354,000 | 26,000 | 16 |
| 1.0 μM | 0.1 μM | 319,000 | 10,000 | 25 |
| 0.5 μM | 0.1 μM | 328,000 | 27,000 | 23 |
| 0.1 μM | 0.1 μM | 347,000 | 38,000 | 18 |
| 0.05 μM | 0.1 μM | 365,000 | 44,000 | 14 |

A comparison of these results with those of Table 1 shows that addition of a mitogen such as ConA increases proliferation by nearly two orders of magnitude. It can be seen that βAED slightly enhanced the proliferative response of spleen cells to ConA, but it did not significantly counteract the depressive effect of 1.0 μM hydrocortisone on proliferation. Although βAED counteracted the effect of 0.1 μM hydrocortisone, the effect was limited in magnitude, since proliferation did not attain the control level.

EXAMPLE 3

Effects of Added βAET and Hydrocortisone on Proliferation in the Presence of a Mitogen Another series of cultures was run in which βAET and/or hydrocortisone was added to cultures similar to those of Example 1 but to which 2.5 μg/ml concanavalin A had been added. The results are set forth in Table 3.

TABLE 3

Influence of BAET and Hydrocortisone on Spleen Cell Cultures
from BALB/c Mice Stimulated with 2.5 µg/ml Concanavalin A

| AET Concentration | Hycort Concentration | Average count (3 samples) | Standard Deviation | % Reduction of Control |
|---|---|---|---|---|
| 5.0 µM | — | 502,000 | 22,000 | incr. 50 |
| 1.0 µM | — | 572,000 | 23,000 | incr. 71 |
| 0.5 µM | — | 523,000 | 29,000 | incr. 56 |
| 0.1 µM | — | 486,000 | 23,000 | incr. 45 |
| 0.05 µM | — | 541,000 | 29,000 | incr. 62 |
| 0.01 µM | — | 553,000 | 35,000 | incr. 65 |
| — | 5.0 µM | 230,000 | 9,000 | 31 |
| — | 1.0 µM | 222,000 | 21,000 | 34 |
| — | 0.5 µM | 221,000 | 22,000 | 34 |
| — | 0.1 µM | 228,000 | 19,000 | 32 |
| — | 0.05 µM | 411,000 | 24,000 | incr. 23 |
| 5.0 µM | 1.0 µM | 547,000 | 51,000 | incr. 63 |
| 1.0 µM | 1.0 µM | 219,000 | 24,000 | 35 |
| 0.5 µM | 1.0 µM | 242,000 | 10,000 | 28 |
| 0.1 µM | 1.0 µM | 223,000 | 17,000 | 34 |
| 0.05 µM | 1.0 µM | 226,000 | 19,000 | 33 |
| 0.01 µM | 1.0 µM | 224,000 | 8,000 | 33 |
| 1.0 µM | 0.1 µM | 405,000 | 42,000 | incr. 21 |
| 0.5 µM | 0.1 µM | 439,000 | 23,000 | incr. 31 |
| 0.1 µM | 0.1 µM | 408,000 | 22,000 | incr. 22 |
| 0.05 µM | 0.1 µM | 419,000 | 31,000 | incr. 25 |
| 0.2% DMSO:EtOH | | 335,000 | 22,000 | — |

It can be seen that βAET markedly enhanced the proliferative response of spleen cells to ConA. In the presence of 1.0 µM hydrocortisone a relatively high dose (5.0 µM) of βAET was required to counteract the depressive effect of the hydrocortisone, while lower doses of βAED showed no significant effect. When 0.1 µM hydrocortisone was present βAET completely counteracted the depressive effect of the hydrocortisone, and mediated an increase to above the control level.

EXAMPLE 4

Effect of βAED and βAET on IL-3 Production

A series of experiments was done to determine whether βAED and βAET would cause a change in the level of the cytokine IL-3. The cultures were prepared in accordance with the general method set out above. After 30 hours the level of IL-3 in the supernatants of the cultures was measured using the IL-3 ELISA kit manufactured by EndoGen Inc., Boston, Mass. The findings are shown in Tables 4 and 5 below.

TABLE 4

EFFECT OF BAED AND BAET ON THE
PRODUCTION OF INTERLEUKIN-3 IN THE
PRESENCE OF 5.0 µg/ml ConA

| AED/AET | Hydrocortisone | IL-3 pg/ml |
|---|---|---|
| 0.2% DMSO:EtOH | | 168 |
| AED 5.0 µM | | 184 |
| AED 0.5 µM | | 180 |
| AET 5.0 µM | | 207 |
| AET 0.5 µM | | 279 |
| | 0.5 µM | 51 |
| AED 5.0 µM | 0.5 µM | 210 |
| AED 0.5 µM | 0.5 µm | 42 |
| AET 5.0 µM | 0.5 µM | 118 |
| AET 0.5 µM | 0.5 µM | 102 |

TABLE 5

| AED/AET | Hydrocortisone | IL-3 pg/ml |
|---|---|---|
| 0.2% DMSO:EtOH | | 30 |
| AED 5.0 µM | | 19 |
| AET 5.0 µM | | 62 |
| AET 0.5 µM | | 100 |
| | 0.5 µM | 1.2 |
| AED 5.0 µM | 0.5 µM | 36 |
| AET 5.0 µM | 0.5 µM | 59 |
| AET 0.5 µM | 0.5 µM | 76 |

The results clearly show that βAET caused increased secretion of IL-3 both in the presence and in the absence of concanavalin-A. Further, they show that hydrocortisone suppressed the production of IL-3 and that βAET counteracted the immunosuppressive effect of hydrocortisone to an extent that brought the level of IL-3 production to nearly the same level as that found in cultures to which no hydrocortisone had been added. Equally interesting was the increase in the level of IL-3 production to higher than normal levels in the cultures to which hydrocortisone had not been added. Hence, it can be said that βAET not only is useful for counteracting the effect of lowering IL-3 levels brought on by corticosteroid therapy, but also that increased production of IL-3 by cells can be induced in cultures by the addition of βAET.

The IL-3 expressed by a culture may be recovered from the media containing IL-3 by known methods such as single or sequential reverse-phase HPLC steps on a preparative HPLC column. (See Urdal, et al., *J. Chromatog.* 296:171 (1984) and U.S. Pat. No. 5,128,450).

EXAMPLE 5

Capsules of a formulation of βAED and dexamethasone for oral administration are prepared containing 15 mg βAED, 5 mg dexamethasone, 150 mg starch, and 5 mg magnesium stearate. The capsules are administered daily or twice a day to achieve a daily dosage of 15 mg and 5 mg dexamethasone per day.

EXAMPLE 6

A preparation for application to the skin or mucosa may be prepared in the following manner:

| Ingredient | % w/w |
| --- | --- |
| AED | 0.5% |
| triamcinolone | 0.5% |
| glyceryl monostearate | 3.0% |
| propylene glycol | 13.0% |
| Petrolatum | 83.0% |

When βAED or βAET or their analogues are administered orally, the active agents may be utilized more efficiently if the active agents are protected from destruction and absorption in the upper gastro-intestinal tract. The active agents are most effective when the period of exposure to the mucosa of the intestinal tract is increased. Hence use of capsules containing the active agents in formulations that effect slow release in the intestine are appropriate for treatment of intestinal disorders such as Crohn's disease and colitis. Use of retention enemas for treatment of inflammation of the large bowel is also appropriate.

EXAMPLE 7

A formulation for administration as a retention enema may be formulated in the following manner:

| Ingredient | w/w % |
| --- | --- |
| BAET | 0.05% |
| desoximetasone | 0.05% |
| Propylene glycol | 99% |

When the active agent is administered to the mucosa of the oral cavity, it may be administered as a spray for use in the oral-pharyngeal cavity and the nasal cavities.

EXAMPLE 8

C57BL/6J mice infected with a single dose of CB4 ($9 \times 10^6$) and treated with βAED plus hydrocortisone or βAED alone. The dosage of βAED was 1 mg βAED in DMSO:ETOH 1:1. The dosage of hydrocortisone was 2 mg administered as a 1% saline solution. Groups of six mice were given the following:

(A) βAED and hydrocortisone (AED/HC) given concurrently with the virus at the same site.

(B) βAED/HC given concurrently with the virus, but at a different site.

(C) βAED/HC given four hours after administration of virus.

(D) βAED only given concurrently with virus at the same site.

The results were as follows:

| Method | Mortality Results |
| --- | --- |
| A | 1/6 |
| B | 6/6 |
| C | 6/6 |

-continued

| Method | Mortality Results |
| --- | --- |
| D | 6/6 |

It can be seen that treatment of the mice concurrently with the infection with a mixture of βAED and hydrocortisone afforded greater protection than did the use of βAED alone.

EXAMPLE 9

Effects of βAED/βAET on Production of IL-2 and IL-3

Murine lymphocytes ($5.0 \times 10^6$) were stimulated with concanavalin A (Con A) 2.5 µg/ml. The effect on IL-2 production of dehydroepiandostrone (DHEA), βAED and βAET was studied. It was found that DHEA suppressed IL-2 production, while AET increased production of IL-2 by about 20%. In media to which hydrocortisone had been added to obtain a concentration of 0.1 µM, it was found that hydrocortisone suppressed production of IL-2 to about 30% of normal (80% suppression) evidenced by the control. The addition of DHEA did not appreciably effect the suppressive activity of hydrocortisone. βAED partially compensated for the decrease in IL-2 resulting from the hydrocortisone, while βAET counteracted the suppressive effect of hydrocortisone, resulting in significant IL-2 release. The table below indicates the comparative effect of βAED and βAET on cytokine production in cell culture.

(TABLE)

| Treatment group | Conc. [µM] | IL-2 Production as % of control | |
| --- | --- | --- | --- |
| | | no hydrocortisone | +hydrocortisone* |
| DHEA | 5.0 | 79.1 | 23.2* |
| | 1.0 | | 26.5* |
| | 0.5 | 82.3 | 29.3* |
| | 0.1 | | 21.2* |
| | 0.005 | 77.5 | 19.7* |
| AED | 5.0 | 96.4 | 39.1* |
| | 1.0 | | 40.9* |
| | 0.5 | 102.3 | 35.5* |
| | 0.1 | | 29.2* |
| | 0.05 | 105.8 | 24.1* |
| AET | 5.0 | 121.7 | 88.9* |
| | 1.0 | | 85.9* |
| | 0.5 | 118.4 | 79.2* |
| | 0.1 | | 65.4* |
| | 0.05 | 119.9 | 64.3* |
| Hydrocortisone | 5.0 | | 20.4 |
| | 1.0 | | 24.5 |
| | 0.5 | | 25.6 |
| | 0.1 | | 22.9 |
| | 0.005 | | 39.1 |

*Hydrocortisone was at 0.1 µM concentration
InterTest-2X from Genzyme ELISA kit for quantification of mouse Interleukin-2.

It can be seen that compared to the control, lymphocytes ($5.0 \times 10^6$ cells/ml) stimulated with concanavalin A (ConA) 2.5 µg/ml will, if treated with hydrocortisone, show suppression of IL-2 levels in the supernatant. When dehydroepiandrosterone (DHEA) is added to the media Containing hydrocortisone the suppression in IL-2 levels occurs to the same extent as in the compositions containing hydrocortisone but no DHEA. However, addition of βAED at a concentration of 0.5 µM to media containing hydrocortisone 0.1 µM resulted in small increases of IL-2 production over that seen when only hydrocortisone was added. Hence, βAED appeared to be able, to some extent overcome the effect of IL-2 suppressive effects of hydrocortisone. However, when βAET was added to media in the absence of hydrocortisone to obtain concentration of 0.5 μM βAET there was an increase of about 20% in IL-2 production. When βAET was added to media at a concentration of 0.5 μM and hydrocortisone concentration was 0.1 μM, the βAET counteracted the effect of the hydrocortisone so that nearly normal levels of IL-2 were produced even in the presence of hydrocortisone.

It is seen, therefore, that 5-androstene 3β,7β,17β-triol exerts an hormonal regulatory effect on multiple cytokines. However, it was noted that the stimulatory effect of IL-2 on cortisol production, an unwanted side effect, was not seen when βAET was administered.

It has been known that both of IL-3 and IL-2 affect cortisol production. The increased production of cortisol in the presence of IL-2 has been considered undesirable. In studies reported in the Joint Journal of Biological Regulators and Homeostatic Agents (October–December 1992 Vol. 6(4), pp 113–115) it was reported that five lung cancer patients were investigated after IL-2 ($3\times10^6$ IU s.c.), after IL-3 administration (1 mcg/kg b.w., I.B) and after administration of both IL-3 and IL-2 by administering IL-3 two hours before IL-2 was injected. IL-2 was shown to stimulate cortisol secretion while IL-3 alone had no effect on cortisol levels. The pretreatment with IL-3 completely neutralized the IL-2 induction of cortisol release.

The discovery that βAET can result in release of IL-2 and IL-3 without concomitant increase in cortisol levels means that βAET can be administered to obtain desirable increase in cytokines without some of the more undesirable side effects. For AET the preferred dosage is usually in the range of 0.001 to 20 mg/da, with 0.001 to 1 mg/da. being the more preferred dosage. However, the dosage will vary depending on the route of administration. Subcutaneous, inhalation and intrathecal administration are methods that would require lower dosages of the active agents.

It has previously been shown (See U.S. Pat. No. 5,128,450) that βAET is effective in counteracting the untoward effects of irradiation and chemo therapies. It is now shown that βAET has the ability to increase IL-2 and IL-3 production without causing increase in cortisol. This provides further evidence that βAET is an important regulator of the body's response to disease, most particularly in regulation of immune response.

I claim:
1. A method of increasing IL-2 and IL-3 levels in a mammal by administration of a composition containing an IL-2 or IL-3 elevating amount of a compound of the formula:

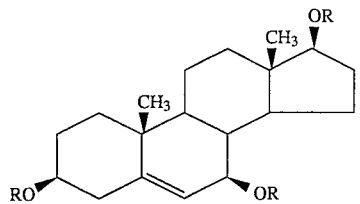

wherein each R individually may be H, alkenyl of 2–8 carbons, alkyl of 1–8 carbons, phenylalkyl of 1–4 carbons, phenyl, or $COR_2$ (acyl), wherein $R_2$ is H, alkyl of 1–8 carbons, alkenyl of 2–8 carbons, phenylalkyl wherein the alkyl has 1–4 carbons or phenyl wherein the phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized.

2. A method of claim 1 wherein the composition is administered subcutaneously.

3. A method of claim 1 wherein the composition is administered transdermally.

4. A method of claim 1 wherein the composition is administered as a patch.

5. A method of claim 1 wherein the composition is administered by inhalation.

6. A method of claim 1 wherein the composition is administered intrathecally.

7. A method of claim 1 wherein the active agent administered is beta-androstenetriol.

8. A method of claim 7 wherein the composition is administered subcutaneously.

9. A method of claim 7 wherein the composition is administered transdermally.

10. A method of claim 7 wherein the composition is administered as a patch.

11. A method of claim 7 wherein the composition is administered by inhalation.

12. A method of claim 7 wherein the composition is administered intrathecally.

* * * * *